US012127964B2

(12) United States Patent
Breuil et al.

(10) Patent No.: US 12,127,964 B2
(45) Date of Patent: Oct. 29, 2024

(54) MEDICAL DEVICE FOR SUPPORTING AT LEAST ONE REGION OF THE BODY

(71) Applicant: THUASNE, Levallois Perret (FR)

(72) Inventors: Laurent Breuil, Unieux (FR); Henri De Moncuit, Bakersfield, CA (US)

(73) Assignee: THUASNE, Levallois Perret (FR)

( * ) Notice: Subject to any disclaimer, the term of this patent is extended or adjusted under 35 U.S.C. 154(b) by 380 days.

(21) Appl. No.: 16/064,523

(22) PCT Filed: Dec. 21, 2016

(86) PCT No.: PCT/FR2016/053610
§ 371 (c)(1),
(2) Date: Jun. 21, 2018

(87) PCT Pub. No.: WO2017/109410
PCT Pub. Date: Jun. 29, 2017

(65) Prior Publication Data
US 2019/0021895 A1    Jan. 24, 2019

(30) Foreign Application Priority Data

Dec. 21, 2015   (FR) ...................................... 1562883

(51) Int. Cl.
*A61F 5/02*        (2006.01)
*A61F 5/01*        (2006.01)
(Continued)

(52) U.S. Cl.
CPC ................ *A61F 5/028* (2013.01); *A61F 5/01* (2013.01); *A61F 5/0111* (2013.01); *A61F 5/02* (2013.01);
(Continued)

(58) Field of Classification Search
CPC .. A61F 5/01; A61F 5/0111; A61F 5/02; A61F 5/022; A61F 5/024; A61F 5/026;
(Continued)

(56) References Cited

U.S. PATENT DOCUMENTS 3,788,366 A * 1/1974 Campbell, Sr. ........... A41F 9/02
                                                    139/421
3,807,162 A * 4/1974 Tsujita ................... D02G 3/328
                                                    57/205
(Continued)

FOREIGN PATENT DOCUMENTS

FR    2156436 A1    6/1973
FR    2934151 A1    1/2010

OTHER PUBLICATIONS

J. Chen, Chapter 4—Synthetic Textile Fibers: Regenerated Cellulose Fibers, Editor(s): Rose Sinclair, In Woodhead Publishing Series in Textiles, Textiles and Fashion, Woodhead Publishing, 2015, pp. 79-95, ISBN 9781845699314, https://doi.org/10.1016/B978-1-84569-931-4.00004-0 (Year: 2015).*

*Primary Examiner* — Caitlin A Carreiro
(74) *Attorney, Agent, or Firm* — Lippes Mathias LLP

(57) ABSTRACT

A medical device for supporting at least one region of the body, and a process for making the medical device. The medical device includes at least one textile panel having a longitudinal direction and a transversal direction, and the textile panel has a woven textile strip, or several woven textile strips at least partially superposed. The woven strip or woven strips each has a warp direction and a weft direction, and has weft threads, first elastic warp threads, second non-elastic warp threads, and third warp threads. The first warp threads and the second warp threads are woven according to a leno shed. The second warp threads form the doup threads. The textile panel is elastic in the longitudinal (Continued)

direction and has a force in the longitudinal direction which is greater than or equal to 500 cN/cm, to achieve an elongation equal to 30%.

15 Claims, 3 Drawing Sheets

(51) Int. Cl.
    *D02G 3/32*     (2006.01)
    *D03D 15/56*     (2021.01)
    *D03D 19/00*     (2006.01)

(52) U.S. Cl.
    CPC ............... *D02G 3/32* (2013.01); *D03D 15/56* (2021.01); *D03D 19/00* (2013.01); *D10B 2509/00* (2013.01)

(58) Field of Classification Search
    CPC .......... A61F 5/028; A61F 5/03; A61F 5/0193; A61F 2013/00119; A61F 2013/00131; A61F 2013/00144; A61F 2013/00148; A61F 2013/00238; A61F 13/00029; A61F 13/00038; D03D 5/00; D03D 7/00; D03D 17/00; D03D 19/00; D03D 15/56; D02G 3/32; D10B 2509/00
    USPC ........ 602/1, 5, 60, 61, 76; 128/100.1, 101.1, 128/845, 876
    See application file for complete search history.

(56) References Cited

U.S. PATENT DOCUMENTS

| | | | |
|---|---|---|---|
| 3,920,054 A | | 11/1975 | Goff, Jr. et al. |
| 3,965,944 A | * | 6/1976 | Goff, Jr. ................. D03D 15/56 139/421 |
| 4,207,885 A | | 6/1980 | Hampton et al. |
| 5,447,498 A | * | 9/1995 | Watson ................... A61F 5/028 128/99.1 |
| 7,886,776 B2 | * | 2/2011 | Jung ................. A61F 13/00038 139/421 |
| 2009/0099497 A1 | * | 4/2009 | Jung ....................... A61F 13/08 602/76 |
| 2014/0303537 A1 | * | 10/2014 | Duport ................... A61F 5/028 602/19 |
| 2017/0266030 A1 | * | 9/2017 | Hess ...................... A61H 7/002 |
| 2018/0085244 A1 | * | 3/2018 | Burke ..................... A61F 13/14 |

* cited by examiner

MEDICAL DEVICE FOR SUPPORTING AT LEAST ONE REGION OF THE BODY

FIELD

The present disclosure relates to the technical field of medical devices for supporting at least one region of the body, comprising at least one elastic textile panel in the longitudinal direction capable of being placed on said region of the body by means of a mechanical tension device of said textile panel multiplying the manual tensioning force of the installer of said at least one textile panel.

BACKGROUND

Medical devices for supporting at least one portion of the body, such as knee or ankle ortheses or lumbar belts, need to be well adjusted to be efficacious. The action of these support devices is linked to a good contention of said region of the body targeted by the prescriber. For example, a patellar kneepad is effective if it properly holds the patella, implying that the kneepad is well adjusted in the region of the calf and thigh. Many patients, unfamiliar with medical support devices, adapt them poorly to their pathologies, either by their morphologies being unsuited thereto, or and above all because they do not understand how to use all the elements of the medical support device.

Also, these medical support devices are often not easy to close while the patient can have problems in comprehension and even observance. In fact, a medical device complicated to handle will not be used and the pathology will not be treated.

Medical support devices of at least one region of the body, such as a lumbar support belt, usually comprise at least one elastic textile panel, that is, capable of elongating in at least one direction under the effect of stress exerted solely manually by the patient and having elastic recovery at least greater than or equal to 90% of its initial length. The elastic textile panel used is generally a fabric comprising elastic weft threads.

Stresses imposed by some standardisation systems, in particular by French social security, ensure that the textile panels of medical support devices must elongate by at least 30% under the effect of minimum force whereof the value is determined according to the type of device. In this way, it is required that lumbar support belts elongate by at least 30% under the effect of a force greater than or equal to 350 cN/cm and the textile panels of strip-lumbar support belts elongate by at least 30% under the effect of a force greater than or equal to 250 cN/cm, with elastic recovery in the both cases having to be greater than or equal to 90% of the initial length of the dimension of the panel which has been stretched. It is therefore necessary to apply force which is greater than or equal to 350 cN/cm or 250 cN/cm respectively for lumbar support belts and textile panels of strip-lumbar support belts to achieve elongation of 30%. The advantage of such devices is that they are pressed neatly onto the region of the body to be supported. However, these devices comprising an elastic textile panel elongating under manual stress alone do not provide a sensation of holding and a sensation of gripping as substantial as those contributed by an inelastic textile, called "rigid", which is applied to the region to be supported by means of a mechanical gripping device multiplying the manual application force of the patient.

Also, it is not possible to combine a mechanical device multiplying the manual application force with an elastic textile panel as the stroke necessary for the device mechanical to achieve grip as substantial as that produced by means of an inelastic textile panel would be excessive. The resulting gripping would therefore not be effective. Also, the mechanical gripping device multiplying the manual placement force would be too complex and bulky to be able to be applied to a medical device intended to be worn by a user. Finally, the gripping time for achieving the compression force required to support said at least one region of the body would be longer than the gripping time necessary in the case of an inelastic textile panel.

There is therefore a need for a medical device comprising at least one textile panel having elastic behaviour in at least one direction, especially capable of elongating by at least 30% of its initial length in said direction with elastic recovery at least greater than or equal to 90% of the initial length which has been stretched, and capable of be placed by means of a mechanical gripping device multiplying the manual application force without elongating, or only of the order of a few percent, to achieve a sensation of gripping and therefore hold equivalent to those provided by inelastic textiles.

SUMMARY

Embodiments of the disclosure relates to a medical device for supporting at least one region of the body, especially knee or ankle orthesis, support belt or support strip, comprising at least one textile panel having a longitudinal direction (L) and a transversal direction (T) arranged so as to encircle all or part of said region of the body to be supported. Said at least one textile panel may comprise a woven textile strip, or several woven textile strips at least partially superposed, said woven strip or said woven strips each having a warp direction (C) and a weft direction (t), and comprising weft threads, first elastic warp threads, second non-elastic warp threads, and third warp threads, said first warp threads and said second warp threads are woven according to a leno shed, the second warp threads forming the doup threads. Also, said at least one textile panel is elastic in the longitudinal direction (L) in that in this direction (L) to achieve elongation equal to 30% it exhibits force which is greater than or equal to 500 cN/cm, in particular measured according to the standard NF EN 14704-1 of June 2005.

It has been found that the combination of first elastic warp threads and second non-elastic warp threads according to a technique called "leno" in a fabric, by exerting considerable traction on said first elastic warp threads so as to take from their reserve of elasticity, produces a woven strip behaving as a textile rigid to being placed under the effect of a manual traction force, but also rigid even if said manual traction force is multiplied by a gripping device multiplying said force. The expression "capable of" or "arranged so as/to" in the present text is equivalent to the following expressions, considered independently of each other: "intended to", "configured to", "adapted to allow" and "adapt to comply with".

The textile panel comprising one or more woven strips also exhibits elastic behaviour under the effect of a substantial traction force which cannot be attained manually, nor even by means of a gripping device multiplying said force to prevent an excessive clamping stroke when said device is being placed.

It is therefore necessary to apply substantial force in the longitudinal direction (L) of the textile panel according to embodiments of the disclosure to achieve elongation greater than or equal to 30%, in particular a force greater than or equal to 500 cN/cm, preferably a force greater than or equal to 700 cN/cm, more preferably greater than or equal to 1000 cN/cm, more preferably greater than or equal to 1000 cN/cm and less than or equal to 2500 cN/cm.

Likewise, the force necessary to elongate the textile panel according to embodiments of the disclosure in the longitudinal direction (L) by 30% is greater than or equal to 500 cN/cm, preferably greater than or equal to 700 cN/cm, more preferably greater than or equal to 1000 cN/cm, more preferably greater than or equal to 1000 cN/cm and less than or equal to 2500 cN/cm.

Even though it is elastic under considerable stress the textile panel according to embodiments of the disclosure provides the patient with a very fine sensation of support and improves his comfort and similarly the observance of the placing of the medical device according to embodiments of the disclosure.

The first elastic warp threads do not turn around another thread but pass above or below the weft threads as is conventional for a warp thread in a fabric. The first elastic warp threads have an arrangement parallel to the warp direction (C) of the woven strip according to embodiments of the disclosure.

Preferably, in the longitudinal direction (L), or the warp direction (C) said textile panel, and especially the or said woven strips, exhibit elongation greater than or equal to 30% under the effect of a force greater than or equal to 700 cN/cm, preferably greater than or equal to 1000 cN/cm, more preferably under the effect of a force greater than or equal to 1000 cN/cm and less than or equal to 2500 cN/cm, or similarly, the force necessary to elongate said textile panel, and especially the or said woven strips, in the longitudinal direction (L), or the warp direction (C), by 30%, is greater than or equal to 700 cN/cm, preferably greater than or equal to 1000 cN/cm, more preferably greater than or equal to 1000 cN/cm and less than or equal to 2500 cN/cm. In particular, said elongations and forces are measured according to the standard NF EN 14704-1 of June 2005.

A textile panel can comprise several superposed woven strips such that the longitudinal edges of the woven strips are parallel to each other or cross according to a determined angle. In particular, the woven strips can be superposed such that the warp directions and wefts (preferably the warp directions) of said strips are parallel to each other or such that the warp or weft direction (preferably the warp direction) of a given strip is displaced according to an alpha angle greater than 0° and under 90° relative to the warp or weft direction (preferably the warp direction) of another woven strip, and preferably the alpha angle is greater than or equal to 30° and less than or equal to 60°. The alpha angle can be for example of the order of 45°.

Preferably, the transversal edges of the superposed woven strips are aligned.

The force necessary to achieve elongation of at least 30% of a textile panel in the longitudinal direction (L) is equal to the sum of forces applied individually to each woven strip entering the composition of said panel so that each of the woven strips elongates by at least 30% in the warp direction (C).

In an embodiment, said at least one woven strip is elastic in the warp direction (C) in that it exhibits elongation greater than or equal to 30% under the effect of a force greater than or equal to 500 cN/cm, preferably greater than or equal to 700 cN/cm, more preferably greater than or equal to 1000 cN/cm and less than or equal to 2500 cN/cm, in particular measured according to the standard NF EN 14704-1 of June 2005; or similarly, said at least one woven strip is elastic in the warp direction (C) in that it exhibits to elongation of 30% an applied force which is greater than or equal to 500 cN/cm, preferably greater than or equal to 700 cN/cm, more preferably greater than or equal to 1000 cN/cm and less than or equal to 2500 cN/cm The standard NF EN 14704-1 dating from June 2005 is incorporated by reference to the present text. This standard is entitled "Determination of the elasticity of fabrics, Part 1: Assays on strip. The principle is that a fabric test piece of specified dimension is stretched at constant speed until either a specified force, or specified elongation for a suitable number of cycles, and its elasticity is determined by measuring several characteristics. The device at constant elongation speed as defined in point 6 of said standard must especially be able to operate at constant elongation speeds, in particular at an elongation speed of 500 mm per minute. The tested fabric test piece can be in a strip (method A) or in a loop (method B), preferably in a strip (method A). The force in cN/cm obtained for having elongation greater than or equal to 30%, in particular of the order of 30%, is calculated by determining the average of forces measured at 30% elongation (or more) over 5 traction cycles. According to a variant, the textile panel comprises a single woven strip.

According to another variant, the textile panel comprises two or three superposed woven strips.

The technique known as "leno" is usually used in the field of prêt-à-porter or decorative articles, for example curtains, such as in the fabric described in U.S. Pat. No. 3,920,054. In this document, an elastic thread and a non-elastic doup thread are displaced in the same tooth of the comb during weaving. The figures show that the non-elastic doup thread makes a turn around the elastic thread for three insertions of weft thread. This weaving technique also known as "leno" or again "doup" creates openwork decors in fabrics.

U.S. Pat. No. 4,207,885 describes the manufacture of a compression bandage using the "leno" weaving technique. The threads 12A and 12B woven according to the technique known as leno are multifilament threads of textured polyamide. During weaving, the warp threads woven according to the leno technique and the other warp threads are put in tension and conventionally fed to the loom, the warp threads woven two-by-two according to the leno technique being more in tension than the other warp threads due to the movement of the doup thread in the warp direction. As it leaves the loom, the woven strip undergoes a thermal removal step for conferring said strip with a certain final extensibility. This bandage is qualified inappropriately as elastic even though it contains no elastic thread.

In terms of the present invention, elastic textile panel or woven strip elastic in a determined manner or direction, means that irrespective of the warp direction and/or the weft direction and/or the longitudinal direction (L), or elastic thread, especially first elastic warp thread and/or third elastic warp thread, that in said longitudinal direction (L) or in said direction, said panel or said woven strip has or said thread has elastic recovery at least greater than or equal to 90%, in particular measured according to the standard NF S97-115 dating from December 2011 combined with the standard NF EN 14704-1 dating from June 2005.

In terms of the present invention, non-elastic textile panel or non-elastic woven strip in a direction (warp or weft) or a determined direction (longitudinal or transversal), in particular in the weft direction (t) or the transversal direction (T), or non-elastic thread, especially second non-elastic warp thread and/or third non-elastic warp thread, means that in said transversal direction (T) or said weft direction (t), or said thread, said panel or said woven strip has elastic recovery less than 90%, in particular measured according to the standard NF S97-115 dating from December 2011 combined with the standard NF EN 14704-1 dating from June 2005.

Preferably, the textile panel and the woven strip according to embodiments of the disclosure are non-elastic respectively in the transversal direction (T) and in the direction weft (t).

In an embodiment, the support device according to embodiments of the disclosure comprises a first end and a second end, the first end comprises a first fastening element and the second end comprises a second fastening element, said first and second fastening elements being capable of cooperating together for their closing and therefore correlatively attaching of said support device to said at least one region of the body to be supported.

The first and second fastening elements can be fastening elements of the loop type and/or hooks, or magnets or any other fastening element known the person skilled in the art.

The medical support device according to embodiments of the disclosure may comprise a mechanical gripping device multiplying the manual application force of said medical support device, especially comprising a gripping device by cable and/or a gripping device by pulley(s).

Preferably, the elastic thread or threads, in particular the first warp thread or the threads, is/are a monofilament thread or threads made of elastane, that is, based on polyurethane, for examples such as those sold under the brand Dorlastan®, Glospan®, Linel®, Creora® or again Lycra®. The elastic thread or threads can be also a monofilament thread or threads made of latex, that is, based on natural or synthetic gum, such as for example elastodiene, or in any other equivalent material known from the prior art. The elastic monofilament thread or threads can also form the elastic core, which is coated or covered by one or more cover threads, preferably such as defined hereinbelow in reference to the spun fibre threads and the multifilament threads.

The weft threads and/or the second non-elastic warp thread(s) and/or the third warp thread(s) is/are selected in the group constituted by a multifilament thread or threads, one of the multifilament thread or threads and a spun fibre thread or threads.

The third warp thread(s) can be elastic or not. If the third warp thread(s) is/are elastic, it/they presents/present preferably according to the same structure and/or the same composition as the first warp thread(s).

Preferably, the third warp thread(s) is/are not elastic.

The weft thread(s) and/or the first warp thread(s), the second warp thread(s) and/or the third warp thread(s), optionally the cover thread(s) can be coloured or transparent according to the preferred aesthetic finish.

The weft threads and/or the or the cover thread(s) of the first warp thread(s) and/or the second warp thread(s) and/or the third warp thread(s) (when not elastic) is/are made of one or more materials selected in the group comprising: polyamide 6, polyamide 6-6, polyamide 12, polypropylene, polyethylene, polyester such as polyethylene terephthalate, cotton, viscose, polyacrylic.

In a variant, the woven strip is made of a fabric having a number of weft threads per centimetre (measured according to the warp direction (C)) less than or equal to 25, more preferably less than or equal to 15.

Number of threads per centimetre, in warp or in weft in the panel woven according to embodiments of the disclosure, means the number of threads on the fabric at rest, in particular after all other thermofixing operations applied to said woven strip as it leaves the loom, per centimetre in the warp direction or weft.

In a variant, one at least of said first warp threads is covered by at least one first cover thread.

This arrangement adjusts the tension applied to the first warp threads to produce a rigid textile panel in terms of the invention but elastic under high stress.

Preferably, said first cover thread forms a number of rpm on said at least one first warp thread between 720 rpm and 1080 rpm.

According to an embodiment, one at least of said first warp threads is covered by a first cover thread and a second cover thread.

Preferably, the second cover thread forms a number of rpm on said at least one first warp thread between 590 rpm and 880 rpm.

In a variant, one at least of said first elastic warp threads, optionally covered by at least one first cover thread (and optionally a second cover thread), has breaking elongation less than or equal to 150%, preferably greater than or equal to 50%, more preferably greater than or equal to 75%.

This breaking elongation can be measured according to the standard NF ISO 2062 dating from 2010, applying especially to synthetic textured threads. This breaking elongation can be measured on said at least one elastic warp thread before being woven or finished.

In the process for making the woven strip according to embodiments of the disclosure, considerable tension is exerted on said at least one first elastic thread so as to take from its elasticity reserve. Said at least one first elastic thread has less elongation in the woven strip than the elongation is exhibits prior to having been implemented by weaving, that is, on its supply spool.

In fact, an elastic thread of the prior art has breaking elongation generally at a minimum of the order of 400% to 500% measured on its supply spool prior to any implementing by weaving.

In a variant, the second warp threads make a turn for insertion of a weft thread.

Preferably, said second warp threads make a turn for insertion of a weft thread over at least one portion of the length in warp of each woven strip.

This arrangement blocks the first elastic warp threads so as to take from their elasticity reserve, that is, diminish their available breaking elongation. In the prior art, the doup thread generally makes a single turn two or three weft threads inserted, while in the present invention the second non-elastic warp threads form one turn for a single insertion of weft thread so as to block and restrict the first elastic warp threads.

In a variant, one at least of said weft threads comprises a thread having a number of filaments greater than or equal to 1 and less than or equal to 5, preferably a number of filaments greater than or equal to 1 and less than or equal to 3, preferably each filament having a diameter greater than or equal to 0.10 mm, especially less than or equal to 0.60 mm, in particular less than or equal to 0.45 mm.

This arrangement favours rigidity of the woven strip in the weft direction but also in the warp direction.

In a variant, the woven strip or several woven strips comprises/comprise alternating solid columns and openwork columns, each of said solid columns and openwork having a longitudinal direction (I) corresponding to the warp direction (C) of said woven strip, the solid columns comprising according to each of their longitudinal edges at least one first warp thread and a second warp thread assembled according to a leno shed.

Preferably, the solid columns comprise the first elastic warp threads, the second non-elastic warp threads, the third warp threads and the weft threads such as defined in the present text.

Preferably, the solid columns and the openwork columns alternate one by one.

Preferably, the solid columns are not openwork compared to openwork columns.

The openwork columns comprise gaps having at least one dimension greater than or equal to 1 mm. These gaps favour discharge of heat and of transpiration of the wearer.

In a variant, the openwork columns are constituted by weft threads.

In a variant, the medical device according to embodiments of the disclosure comprises a multiplier gripping device of the manual application force of said at least one textile panel, especially a mechanical gripping device comprising a gripping device by cable and/or a gripping device by pulley(s). This multiplier gripping device multiplies the manual placement force of said at least one textile panel by two, three, or even more.

According to a second aspect, the invention relates to a process for manufacture of a device according to any one of the preceding variant embodiments in reference to a first aspect, comprising the following steps:
- a first weaving step of a woven textile strip, or several woven textile strips, each textile strip being woven with first elastic warp threads, second non-elastic warp threads, third warp threads, and weft threads, the first warp threads and the second warp threads being woven according to a leno shed such that the second threads form the doup threads;
- a tension application step (daN) to one at least of said first elastic warp threads, preferably to all the first elastic warp threads, so as to elongate said at least first elastic warp thread during said first step;
- a shaping step of a textile panel having longitudinal (L) and transversal (T) directions comprising a woven textile strip, or several woven textile strips superposed, in the longitudinal direction (L) to achieve elongation equal to 30%, said textile panel having a force which is greater than or equal to 500 cN/cm, in particular measured according to the standard NF EN 14704-1 of June 2005.

In a sub-variant, said woven textile strip or said woven textile strips undergoes/undergo a finishing step.

In a preferred embodiment, said finishing step of the woven textile strip comprises the following steps:
- a first step of thermal post-processing consisting of dipping the woven strip in a bath of hot water for at least one second, preferably for at least 15 second, the temperature of the water of said bath being preferably greater than or equal to 60° C.; or
- a first step of thermal post-processing consisting of dipping the woven strip in a bath of water at ambient temperature (preferably whereof the temperature is greater than or equal to 10° C. and less than or equal to 30° C.), said bath comprising at least one additive, said additive being selected preferably so as to attribute rigidity ("main" to the woven strip) or flexibility; and then
- a second step of thermal post-processing consisting of moving the woven strip into a processing chamber containing hot air, or humid air, preferably the temperature of the air being greater than or equal to 60° C. (and less than or equal to 150° C.), then calandering said woven strip by moving it to at least one heated cylinder, especially to all heated cylinders, to achieve its dimensional shrinkage.

Said at least one additive can be a polymer of silicone or polyurethane. The person skilled in the art knows which additives to select to impart rigidity or flexibility to a woven textile strip.

Also, the external surface of the cylinder or cylinders during calandering of the second step thermal post-processing can be metallic, and/or optionally coated by enduction in a non-adherent polymer, for example a fluorinated polymer such as PTFE. The person skilled in the art knows how to adjust the temperature of the cylinder or said cylinders as well as their rotation speed(s) so as to achieve relaxation of the textile strip and dimensional shrinkage of the latter.

This post-processing step gives the fabric its final mechanical characteristics, due to shrinkage of the different threads constituting the fabric. The variant embodiments realisation and definitions described above in reference to the first aspect of the invention also apply to the process.

In a variant, the tension application step (daN) consists of applying tension to one at least of said first elastic warp thread or said threads by means of one or more devices selected in the group comprising the following devices: one at least of said first elastic warp threads is covered by at least one first cover thread having a number of rpm greater than or equal to 720 rpm, and/or a tension exerted on one at least of said first elastic warp threads greater than or equal to 10 cN, and/or a number of turns of the second warp threads equal to one for insertion of a weft thread.

The tension exerted on a thread (measured in cN) can be measured for example by means of a tensiometer.

DETAILED DESCRIPTION OF DIAGRAMS

The present invention will be better understood from the following embodiments, cited by way of non-limiting example, illustrated by the following figures annexed to the present, and in which.

DESCRIPTION OF EMBODIMENTS

Figure 1:
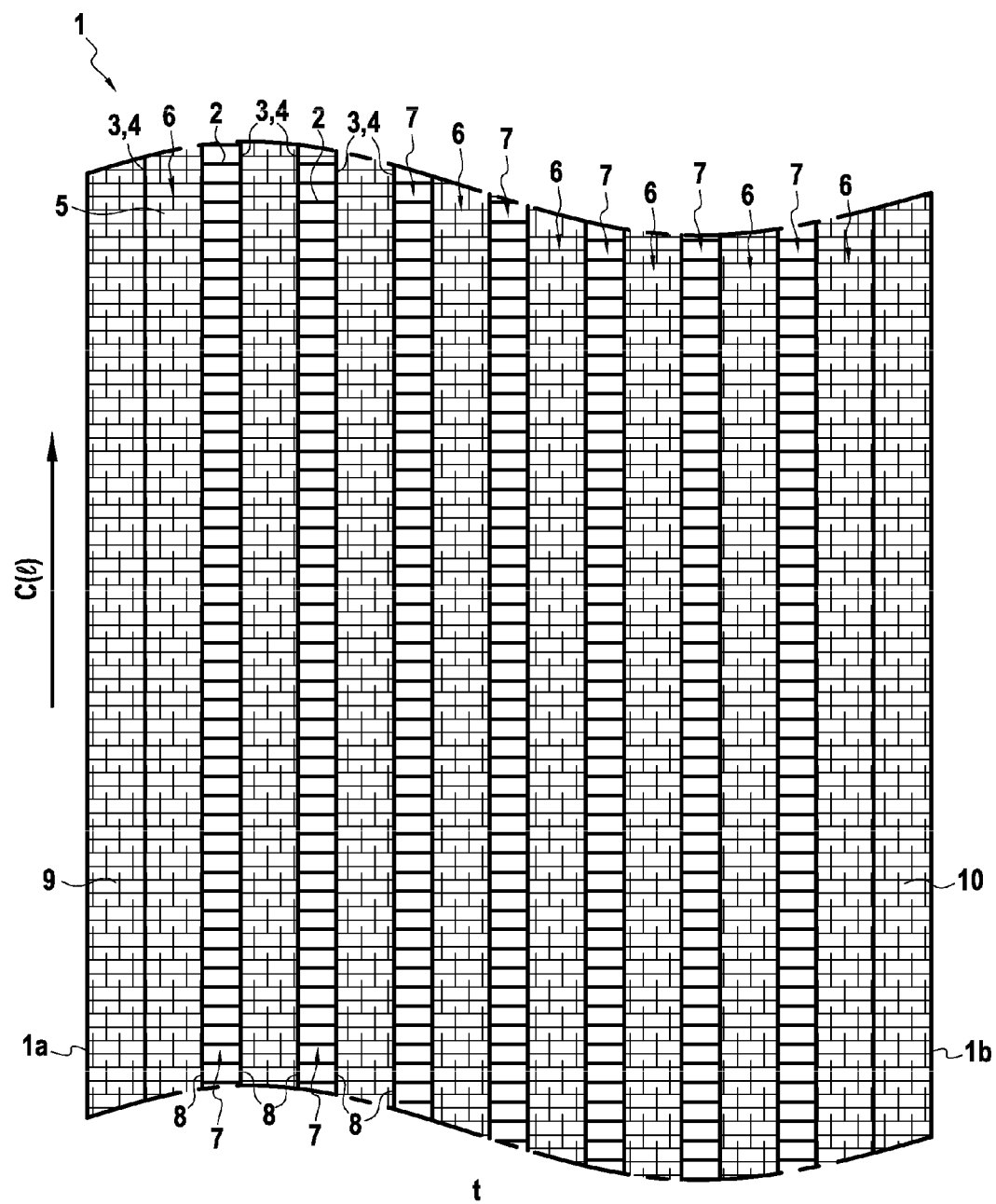
FIG. 1 is a schematic illustration of a first example of a woven strip according to embodiments of the disclosure.

The woven textile strip 1 according to embodiments of the disclosure shown in FIG. 1 has a warp direction C and a weft direction t. Said woven strip 1 is a fabric comprising weft threads 2, first elastic warp threads 3, second non-elastic warp threads 4, and third warp threads 5, said first warp threads 3 and said second warp threads 4 are woven according to a leno shed the second warp threads 4 forming the doup threads. Said woven strip 1 is elastic in the warp direction C and in the warp direction, in this very example, exhibits elongation greater than or equal to 30% under the effect of a force greater than or equal to 700 cN/cm, in particular measured according to the standard NF EN 14704-1 of June 2005. In this way, to achieve elongation by 30% in the longitudinal direction L, it is required to apply to apply a force greater than or equal to 700 cN/cm to said textile panel in this direction L.

The woven strip 1 comprises alternating solid columns 6 and openwork columns 7, each of said solid columns 6 and openwork 7 having a longitudinal direction I corresponding to the warp direction C of said woven strip 1. Preferably, each of the solid columns 6 comprises on each of its longitudinal edges 8 at least one first elastic warp thread 3 and a second non-elastic warp thread 4 woven according to a leno shed.

The openwork columns 7 comprise weft threads 2 extending in the direction weft t, transversally to the warp direction C.

The woven strip 1 comprises according to each of its longitudinal edges 1a,1b respectively a selvedge 9,10.

Figure 2:
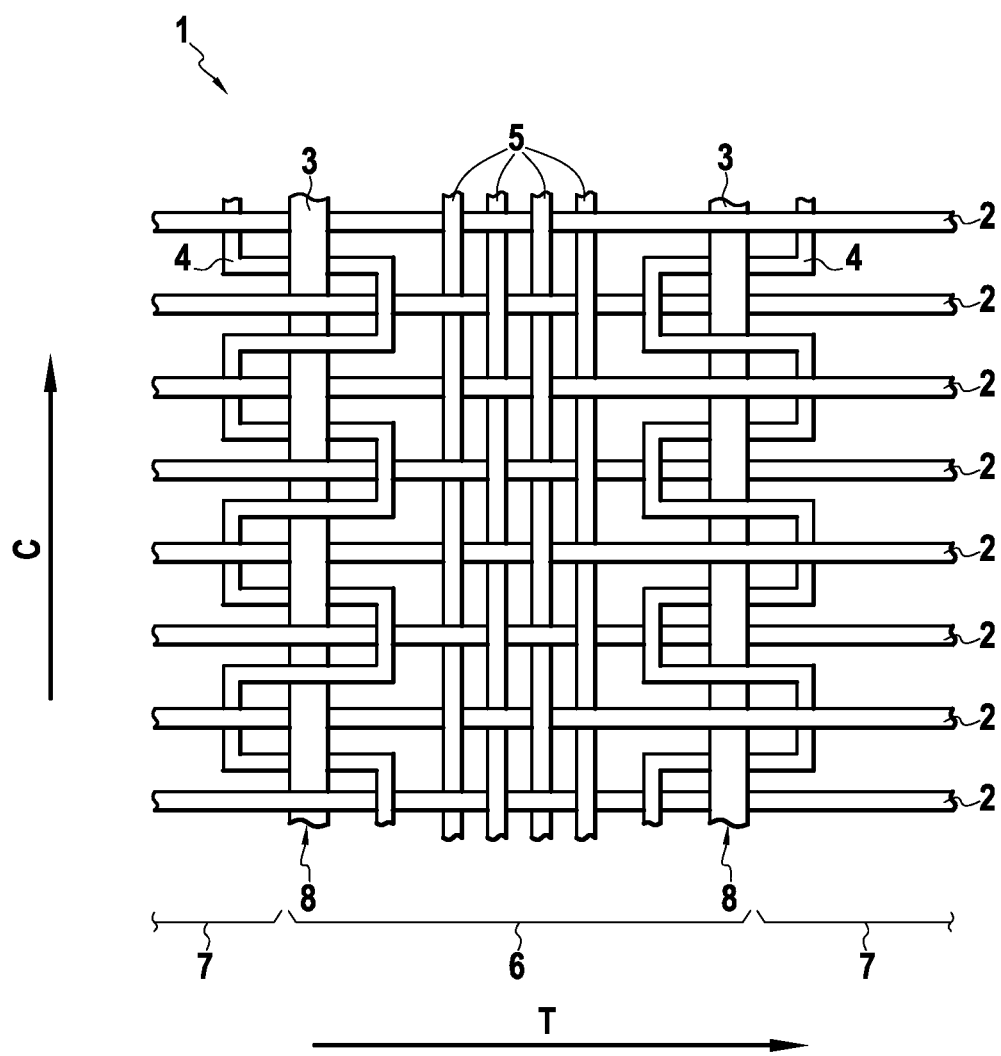
FIG. 2 is a schematic illustration of the arrangement of the threads of a solid column between two openwork columns of the woven strip shown in FIG. 1.

FIG. 2 schematically illustrates a solid column 6 comprising on each of its longitudinal edges 8 a first elastic warp thread 3 and a second non-elastic warp thread 4 woven together according to a leno shed. The solid column 6 is displaced between two openwork columns 7 constituted by the weft threads 2. The solid column 6 comprises third warp threads 5 displaced between the first 3 and second 4 warp threads woven according to a leno shed.

Preferably, and as is evident in FIG. 2, the second warp threads 4 make a turn about the first warp threads 3 for insertion of a weft thread 2. Preferably, one at least of said weft threads 2 is a thread comprising a number of filaments greater than or equal to 1 and less than or equal to 5, preferably comprising a number of filaments greater than or equal to 1 and less than or equal to 3, in this very example equal to 3, preferably each filament having a diameter greater than or equal to 0.1 mm.

In this very example, in the warp direction C said woven strip 1 exhibits elongation greater than or equal to 30% with application of a force greater than or equal to 700 cN/cm. In this way, to achieve elongation of 30% in the longitudinal direction L, it is required to apply a force greater than or equal to 700 cN/cm to said strip 1 in this direction L.

Preferably, the third warp threads 5 and the second warp threads 4 are not elastic and are for example multifilament threads or threads spun from fibres having a titre greater than or equal to 50 dtex and less than or equal to 500 dtex, for a number of filaments between 10 and 300.

The first 3, second 4 and third 5 warp threads as well as the weft threads 2 can be transparent or coloured. Also, said threads can be made of polyamide 6, polyamide 6-6, polyester, polyethylene terephthalate, polypropylene, cotton, or any other natural or synthetic or artificial non-elastic material.

Figure 3:
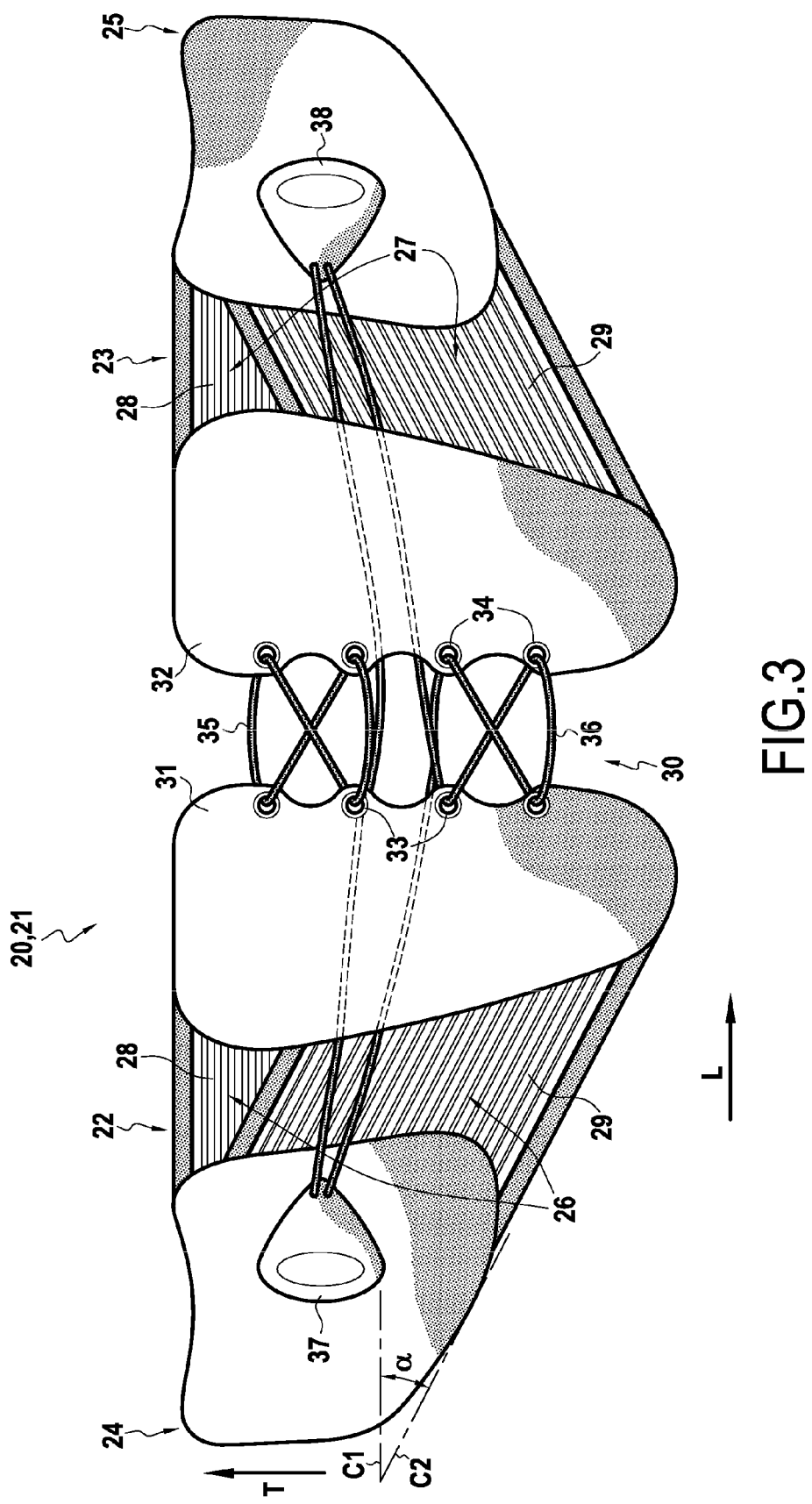
FIG. 3 is a schematic illustration seen according to its posterior face of a first example of a medical device according to embodiments of the disclosure comprising two textile panels, each textile panel comprising two woven textile strips such as the woven strip shown in FIG. 1, said medical device is in this example specified as a lumbar support belt.

FIG. 3 shows a medical device 20 according to the disclosure for supporting at least one region of the body. In this very example, this is a lumbar support belt 21. Said medical device 20 comprises a lateral left part 22 and a lateral right part 23 intended, in operation and therefore when worn, to cover respectively the left flank and at least one left posterior dorsal portion, and the right flank and at least one right posterior dorsal portion of the wearer.

The medical device 20 comprises a first end 24 and a second end 25 provided respectively with a first fastening element and a second fastening element, said first and second fastening elements being capable of cooperating to allow closing of the lumbar support belt 21 on the torso of the wearer. Said first and second fastening elements are for example respectively fastening hooks and a textile having fastening loops.

Each lateral part 22,23 of the device 20 comprises respectively a textile panel 26,27 according to the disclosure. Each textile panel 26,27 comprises respectively two woven strips 28, 29 each corresponding to the woven strip 1 shown in FIG. 1. The woven strips 28,29 are superposed and arranged with respect to each other such that the warp direction C1 of the woven strip 28 forms an alpha angle of the order of 45° with the warp direction C2 of the woven strip 29.

In the longitudinal direction each textile panel 28 and 29 has an elongation greater than or equal to 30% under the application of a force greater than or equal to 700 cN/cm, especially between 1400 cN/cm and 2000 cN/cm. It is therefore necessary to apply force of between 1400 cN/cm and 2000 cN/cm in the longitudinal direction of said textile panels 28,29 to achieve elongation of at least 30% in this direction L.

The medical device 20 also comprises a mechanical multiplier gripping device of the manual application force 30 displaced between the lateral left 22 and right 23 parts. In this very example, this multiplier gripping device 30 comprises first 31 and second 32 lateral portions each comprising several eyelets 33,34, in particular four eyelets, for the passage of two slender elements 35,36, such as cords. The eyelets 33 and the eyelets 34 respectively lateral first 31 and second 32 portions are opposite so as to form multiple references of the slender elements 35,36 multiplying the placement force. Two prehension members 37,38, especially two handles, are attached via the slender elements 35,36 to said mechanical gripping device 30 and can be actuated by the installer to place the lumbar support belt 21 on his back and grip the latter so as to have said first and second fastening elements cooperate together for closing of said medical device 20.

During operation, the patient places the lumbar support belt 21 on his torso, actuates the multiplier gripping device 30 by pulling on the handles 37,38 so as to press and clamp the belt 21 on his back, then has the first and second fastening elements cooperate to connect the belt 21. The textile panels 26,27, even though elastic in the longitudinal direction L under considerable stress, cooperate during placing and use with said multiplier gripping device 30, such as rigid textile panels. In this way, the elongation achieved even under the manual force multiplied by said textile panels 26,27 in the longitudinal direction L is minimal, for example of the order of a few percent (2 to 5%) without a considerable clamping stroke.

Where any standards of national, international, or other standards body are referenced (e.g., ISO, etc.), such references are intended to refer to the standard as defined by the national or international standards body as of the priority date of the present specification. Any subsequent substantive changes to such standards are not intended to modify the scope and/or definitions of the present disclosure and/or claims.

Even though some features, concepts or aspects of the embodiments may be described herein as being a preferred (more or less) arrangement or method, such description is not intended to suggest that such feature is required or necessary unless expressly so stated.

The invention claimed is:

1. A medical device for supporting at least one region of the body, wherein said medical device is a support belt, said support belt comprising at least one textile panel having a longitudinal direction and a transversal direction arranged so as to encircle all or part of the at least one region of the body to be supported, wherein said at least one textile panel comprises a woven textile strip A and a woven textile strip B at least partially superposed, said woven strip A having a warp direction A and a weft direction A and said woven strip B having a warp direction B and a weft direction B, wherein the warp direction A and the warp direction B cross each other at an angle alpha greater than 0° and under 90°, and each of the woven textile strips A and B comprising weft threads, first elastic warp threads, second non-elastic warp threads, and third warp threads, wherein said first elastic warp threads and said second non-elastic warp threads are woven according to a leno shed, the second warp threads forming doup threads, wherein at least one weft thread comprises between 2 and 5 filaments, each filament having a diameter greater than or equal to 0.10 mm, wherein at least one of the woven strips A and B has a number of weft threads per centimetre less than or equal to 25, wherein said at least one textile panel is elastic in the longitudinal direction and has a force in the longitudinal direction which is greater than or equal to 1000 cN/cm, to achieve an elongation equal to 30%, wherein at least one of said first elastic warp threads comprises at least one elastic monofilament core thread made of elastane or latex, coated or covered by at least a first cover thread;

wherein the device comprises a multiplier gripping device of a manual application force of said at least one textile panel, said multiplier gripping device is a mechanical gripping device by cable and/or by pulley.

2. The device according to claim 1, wherein the woven textile strip A and woven textile strip B each comprises alternating solid columns and openwork columns, each of said solid and openwork columns having a longitudinal direction corresponding to the warp direction of the respective woven textile strip, the solid columns comprising at least one first warp thread and a second warp thread assembled according to a leno shed.

3. The device according to claim 2, wherein the openwork columns are constituted by weft threads.

4. The device according to claim 1, wherein said at least one first cover thread forms a number of rotations per meter on said elastic monofilament core thread higher than or equal to 720.

5. The device according to claim 1, wherein at least one of said first elastic warp threads has a breaking elongation less than or equal to 150%.

6. The device according to claim 1, wherein the second non-elastic warp threads make a turn around the first elastic warp threads for one insertion of a weft thread.

7. The device according to claim 1, wherein at least one of the woven strips A and B has a number of weft threads per centimetre less than or equal to 15.

8. The device according to claim 1, wherein the at least one weft thread comprises 2 or 3 filaments, each filament having a diameter greater than or equal to 0.10 mm.

9. The device according to claim 1, wherein the force is greater than or equal to 1000 cN/cm and less than or equal to 2500 cN/cm.

10. The device according to claim 1, wherein said device comprises a second cover thread that coats or covers said elastic monofilament core thread and forms a number of rotations per meter on said elastic monofilament core thread that is higher than or equal to 590.

11. The device according to claim 1, wherein said at least one textile panel behaves like a rigid textile panel under the effect of a manual traction force.

12. The device according to claim 1, wherein said at least one first elastic warp thread, comprising at least one elastic monofilament core thread made of elastane or latex, coated or covered by at least a first cover thread, has breaking elongation greater than or equal to 50%.

13. The device according to claim 1, wherein said at least one first cover thread forms a number of rotations per meter on said elastic monofilament core thread between 720 and 1080.

14. A manufacturing process of a device according to claim 1, the manufacturing process comprising the following steps:

a first weaving step of a woven textile strip A and of a woven textile strip B, said woven textile strip A having a warp direction A and a weft direction A and said woven textile strip B having a warp direction B and a weft direction B, each of the woven textile strips A and B being woven with first elastic warp threads, second non-elastic warp threads, third warp threads, and weft threads, the first elastic warp threads and the second non-elastic warp threads being woven according to a leno shed such that the second non-elastic threads form doup threads;

wherein at least one weft thread comprises between 2 and 5 filaments, each filament having a diameter greater than or equal to 0.10 mm;

wherein at least one of the woven strips A and B has a number of weft threads per centimetre less than or equal to 25;

a tension application step (daN) on at least one of said first elastic warp threads so as to elongate said at least one first elastic warp thread during said first weaving step;

a shaping step of at least one textile panel having a longitudinal direction and a transversal direction comprising said woven textile strips A and B at least partially superposed in a manner that the warp direction A and the warp direction B cross each other at an angle alpha greater than 0° and under 90°;

wherein said at least one textile panel has in the longitudinal direction a force which is greater than or equal to 1000 cN/cm to achieve elongation equal to 30%, and wherein at least one of said first elastic warp threads comprises an elastic monofilament core thread made of elastane or latex, coated or covered by at least a first cover thread.

15. The manufacturing process according to claim 14, wherein the tensioning application step consists of exerting tension on at least one of said first elastic warp threads wherein at least one of said first elastic warp threads is covered by at least one first cover thread having a number of rotations per meter greater than or equal to 720-rotations per meter, and/or tension exerted on at least one of said first elastic warp threads is greater than or equal to 10 cN, and/or a number of turns of the second non-elastic warp threads around the first elastic warp threads is equal to one for an insertion of a weft thread.

* * * * *